(12) United States Patent
Stec et al.

(10) Patent No.: US 10,117,644 B2
(45) Date of Patent: Nov. 6, 2018

(54) ELECTROPHYSIOLOGICAL DIAGNOSTIC CATHETER ESPECIALLY FOR OBTAINING OF ENDOMYOCARDIAL BIOPSY OF HEART TISSUE

(71) Applicant: Medidata Sp. z o.o., Warsaw (PL)

(72) Inventors: Sebastian Stec, Warszaw (PL); Sanjeev Choudhary, Warsaw (PL); Janusz Sledz, Skarzysko-Kamienna (PL)

(73) Assignee: MEDIDATA SP. Z O.O., Warsaw (PL)

( * ) Notice: Subject to any disclaimer, the term of this patent is extended or adjusted under 35 U.S.C. 154(b) by 287 days.

(21) Appl. No.: 14/900,118

(22) PCT Filed: Mar. 12, 2015

(86) PCT No.: PCT/IB2015/051811
§ 371 (c)(1),
(2) Date: May 12, 2016

(87) PCT Pub. No.: WO2016/071778
PCT Pub. Date: May 12, 2016

(65) Prior Publication Data
US 2016/0324510 A1   Nov. 10, 2016

(51) Int. Cl.
*A61B 5/00* (2006.01)
*A61B 10/06* (2006.01)
*A61B 5/042* (2006.01)
*A61B 5/06* (2006.01)

(52) U.S. Cl.
CPC .............. *A61B 10/06* (2013.01); *A61B 5/042* (2013.01); *A61B 5/0422* (2013.01); *A61B 5/6852* (2013.01); *A61B 5/065* (2013.01)

(58) Field of Classification Search
CPC ....... A61B 5/042; A61B 5/0422; A61B 5/053; A61B 5/0536; A61B 5/0538; A61B 5/6852; A61B 10/02; A61B 10/04; A61B 10/0266; A61B 10/06
See application file for complete search history.

(56) References Cited

U.S. PATENT DOCUMENTS

| | | | |
|---|---|---|---|
| 5,779,646 A * | 7/1998 | Koblish | A61B 18/1445 600/567 |
| 6,701,176 B1 | 3/2004 | Halperin et al. | |
| 6,738,655 B1 * | 5/2004 | Sen | A61B 5/0422 600/374 |
| 9,107,599 B2 * | 8/2015 | Harlev | G16H 10/60 |
| 9,757,036 B2 * | 9/2017 | Strommer | G16H 50/50 |
| 9,820,677 B2 * | 11/2017 | Olson | A61B 5/066 |

(Continued)

FOREIGN PATENT DOCUMENTS

| WO | 2008 121143 A1 | 10/2008 |
|---|---|---|
| WO | 2011 0041489 A2 | 4/2011 |

*Primary Examiner* — Max Hindenburg
(74) *Attorney, Agent, or Firm* — Andrew W. Chu; Craft Chu PLLC

(57) ABSTRACT

The electrophysiological diagnostic catheter obtains an endomyocardial biopsy of heart tissues. The catheter includes a manipulation handgrip, main channel, distal ring and diagnostic rings connected with electrical connections. There is a centrally located, open internal channel, wherein inlet/outlet of internal channel is located in the distal ring, or is guided and monitored using a system for 3D electroanatomical mapping.

10 Claims, 6 Drawing Sheets

(56) References Cited

U.S. PATENT DOCUMENTS

| | | | |
|---|---|---|---|
| 9,867,661 B2 * | 1/2018 | Werneth | A61B 18/1492 |
| 2005/0010095 A1 | 1/2005 | Stewart et al. | |
| 2007/0049817 A1 | 3/2007 | Preiss et al. | |
| 2009/0209950 A1 | 8/2009 | Starksen | |
| 2011/0087175 A1 | 4/2011 | Krishnan | |

* cited by examiner

ELECTROPHYSIOLOGICAL DIAGNOSTIC CATHETER ESPECIALLY FOR OBTAINING OF ENDOMYOCARDIAL BIOPSY OF HEART TISSUE

CROSS-REFERENCE TO RELATED APPLICATIONS

See also Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

An object of the invention is electrophysiological diagnostic catheter especially for obtaining of endomyocardial biopsy of heart tissue, which is led and monitored using 3D electroanatomical mapping system.

The invention relates to diagnostic procedure of heart muscle biopsy (—endomyocardial biopsy—EMB), which is an invasive procedure giving a possibility to carry out morphological, immunohistological and structural examination.

2. Description of Related Art Including Information Disclosed Under 37 CFR 1.97 and 37 CFR 1.98

Heart muscle biopsy is performed in case of specific heart illnesses, such as unexplained congestive heart failure, sarcoidosis, amyloidosis, or storage diseases. An indication for biopsy is also a suspicion of neoplastic processes, giant-cell myocarditis, not responding to treatment and idiopathic acute heart failure, heart failure in individuals with cosinophilia, arrythmia, suspicion of arrythmogenic cardiomyopathy, conduction disorders (especially II and III-degree atrioventricular block) and necessity of transplanted heart examination for possible rejection. During EMB there are taken 3 to 10 samples from the right or/and left ventricle.

From the state of the art there are devices known used in cardiology, which comprise elements enabling imaging, these are most often cameras or scanners or other devices used for detection or other devices including forceps.

From the application Nr. WO10102794A1 there are solutions known, which relate to the conducting diagnostic and/or therapeutic procedures, wherein a device comprises hollowed tube catheter for placement in vein or artery or other parts of body, wherein catheter is equipped with ending and imaging device is connected with catheter ending. Besides, the device comprises additional clearance or other tube elements around or in vicinity of catheter, through which guidewires, stents, balloons or other therapeutic modalities can be introduced, e.g. in order to examine or treat stenosis of coronary arteries or occlusions. Devices can also comprise biopsy pliers, an electrode catheter and mapping, ablative head or guidewires or any other device for usage in other diagnostic and/or therapeutic procedures.

From the US2008130965A application, there is a device known, comprising: a surgery device, having at least one or more sensors, wherein at least part of the sensors can detect orientation and location data, and at least a part can detect surgical parameters in situ. The surgical device includes at least one or more devices: an autonomous device, probe, guide, catheter, stimulator, aspirator, pliers, microscope, endoscope, and one or more implants.

Solutions from W008121143A1 relate to a catheter system with imaging possibilities to introduce a device into the desired location in patient's body. This catheter comprises inter alia an imaging scanner for imaging within whole patient's body, and an imaging reader, which is located inside and on distal ends of said elastic wire to enable imaging at least in one position.

From application Nr. RU2173091 a method of intravenous endomyocardial electrode catheter introduction is known, the system having bioptome installed on the end of catheter in order to examine and obtain tissue samples. Endomyocardial catheters and bioptome are designed as a cylinder of opposite spiral narrow fastening elements of crescent shape. The device is introduced to heart tissue, by rotating around its axis under electrographic control until moment of amplitude increases up to 70-120% in relation to its initial value and change in curve shape from two-phase to specific one-phase curves. Tissue samples are obtained by expanding of catheter-electrode. Thanks to that, it is possible to obtain tissue samples from different heart regions, even from the right ventricle.

There are also other devices known, in form of catheters capable of electroanatomic mapping, which most often additionally comprise ablation head, as described in the US2007287902A application, where a method of visual support in usage of electrophysiological catheter in heart is described, covering visualisation of 3D electroanatomical mapping, based on data delivered during usage of catheter of heart region which is intended for treatment, recording of 3D visual data from corpus region comprising region subjected to treatment using method of tomographic 3D imaging, separation of at least a significant part of region being treated based on 3D image and correlation and visualisation of data from 3D electroanatomical mapping and selection of 3D images next to each other in correct position and dimensions. Operators can also perform ablation treatment.

Despite development of tools for heart muscle biopsy (EMB), EMB diagnostic value is not satisfactory because of lack of targeted biopsy of pathological regions. Introduction of systems for a 3D electroanatomical mapping (3D-EAM) caused a possibility of creation of three-dimensional potential maps, which allow to identify heart regions with pathological electric function. EAM systems enable 3D EAM formation with mono- and bipolar potential map which reproduces region of borderline zone, scar and healthy muscle from the endocardium side and predicting potential pathological regions in a region of deeper myocardium and epicardium. Additional 3D mapping allows to define a conduction system and valve region, which can be linked with avoidance of performing biopsy from a conduction system surrounding/valve system and complications connected with that. Besides, EMB based on bioptome sampling from endocardium with amplitude <1.5 mV (scar or pathological fibrosis suspicion) can give crucial and more reliable information on pathological process in heart muscle and possibilities of further treatment. Especially important groups of patients are patients with cardiac arrhythmia and suspicion of myocarditis. EAM in those patient populations allows for performance of more precise biopsies from regions of disorders of electrophysiological heart muscle potentials. Up to now, EAM-EMB was based on the use of separate device for EAM and EMB. To create EAM map, mapping electrode was used and additionally biopsy specimen was introduced to EMB.

BRIEF SUMMARY OF THE INVENTION

Solution according to the invention relates to one, universal device for performance of EAM and consequent EMB. This is an electrode combining properties of electrophysiological electrode (EP—potencies registration, stimulation and generation of potential maps in 3D-EAM) and biopsy specimens for EMB enabling for simultaneous 3D-EAM and carrying out of EMB guided by that.

The electrophysiological diagnostic catheter, according to invention, is composed of two elements combined together in one part: controlled electrophysiological electrode in the form of catheter and bioptome—controlled forceps intended for direct tissue sampling from heart, being able to insert into the heart through channel located inside catheter, which are additionally controlled and monitored using system for three-dimensional electroanatomical mapping.

The electrophysiological diagnostic catheter is also composed of electrical wires combined with diagnostic rings and a distal ring and manipulation handgrip with a mechanism controlling the distal end of the catheter and with electrical connections.

Bioptome is composed of controlled forceps for tissue sampling, tension members and a shield housing system enabling forceps control and introduction of them into the interior of the electrophysiological diagnostic catheter and hinge mechanism.

The electrophysiological diagnostic catheter should be registered as a whole in X-rays, but usage of electrophysiological rings enables usage in any 3D-EAM system with reduction or elimination of X-rays.

The object of the invention is electrophysiological diagnostic catheter in particular to obtain endomyocardial biopsy of heart tissues, comprising a manipulation handgrip, a main channel, a distal ring and diagnostic rings, connected with an electric connection characterized in that it comprises:
  a centrally located, open internal channel, wherein inlet/outlet of internal channel is located in distal ring; and is guided and monitored using system of electroanatomical 3D mapping.

Preferably, the internal channel is unobstructed in both ways.

Preferably, the inlet/outlet of internal channel is equipped with round, cut external edges, which create an arch after placement of bioptome in the internal channel in stand-by position.

Preferably, edges of distal ring with bioptome in internal channel in stand-by position are atraumatic.

Preferably, in manipulation handgrip there are placed: inlet/outlet for electric connections; and inlet/outlet for central channel.

Preferably, electrophysiological diagnostic catheter comprises diagnostic rings in the amount of 4 to 20 pieces.

Preferably, the internal channel is surrounded by electric wires connecting diagnostic rings and distal ring with the manipulation handgrip, which are connected to the electrophysiological system.

Preferably, bioptome is introduced/outputted through internal channel.

Preferably, jaws of bioptome forceps overlap alternately creating atraumatic, rounded ending.

Preferably, length of tendons connecting forceps with mechanism controlling bioptome is the same as length of catheter.

Preferably, the electrophysiological diagnostic catheter in distal end region of the catheter in internal channel is equipped with a blocking mechanism.

Preferably, bioptome below the jaws of forceps comprises a blocking mechanism.

Preferably, the blocking mechanism is a thread, which allows to perform at least half of a turn.

Preferably, proximal gap of the internal channel ends with a valve.

The advantage of the invention is a combination of the electrophysiological catheter properties (potencies registration, stimulation and generation of potential maps in 3D-EAM) and bioptome for EMB, enabling for simultaneous 3D-EAM and carrying out of EMB guided by this way.

Usage of the 3D EAM system for myocardium sampling for examination enable fast diagnostics of lesions in the heart region and explanation of causes of e.g. arrhythmias or causes of heart failure. Solutions according to the invention enable to perform treatment using one venopunction (right) or arteropunction (left ventricle) using the same type of device.

BRIEF DESCRIPTION OF THE SEVERAL VIEWS OF THE DRAWINGS

The electrophysiological diagnostic catheter according to the invention was described in more details in exemplary embodiments and on the drawings.

DETAILED DESCRIPTION OF THE INVENTION

Figure 1:
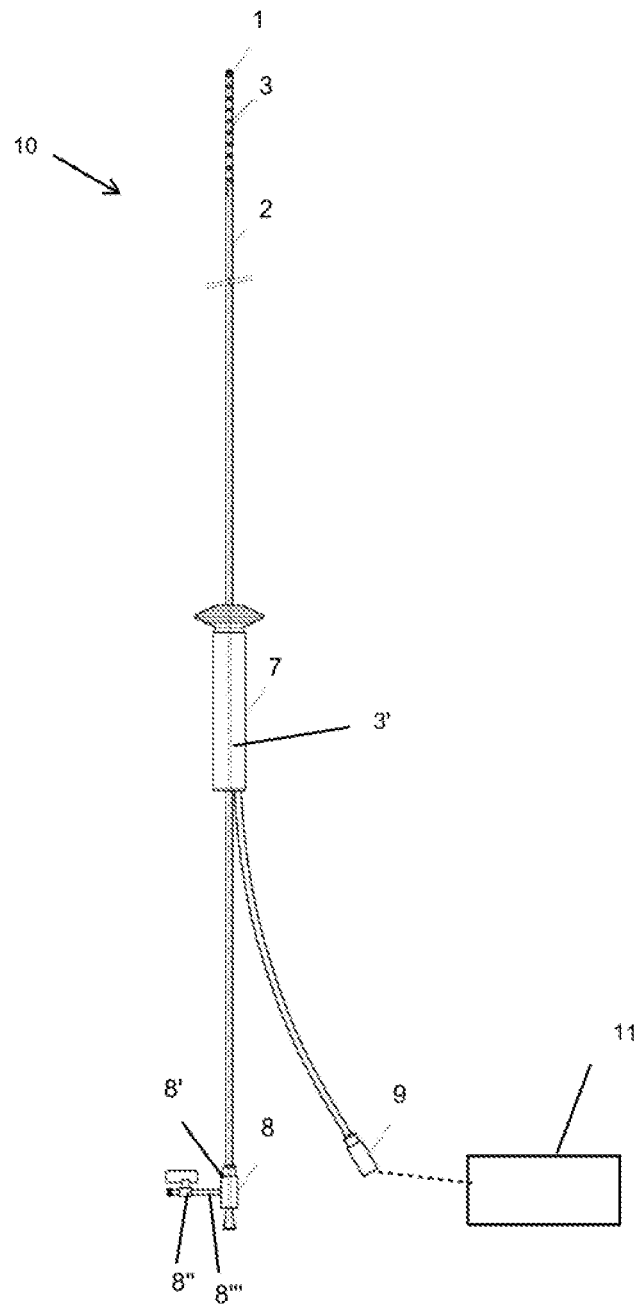
FIG. 1 shows a top plan view from the top on electrophysiological diagnostic catheter.
Figure 2:
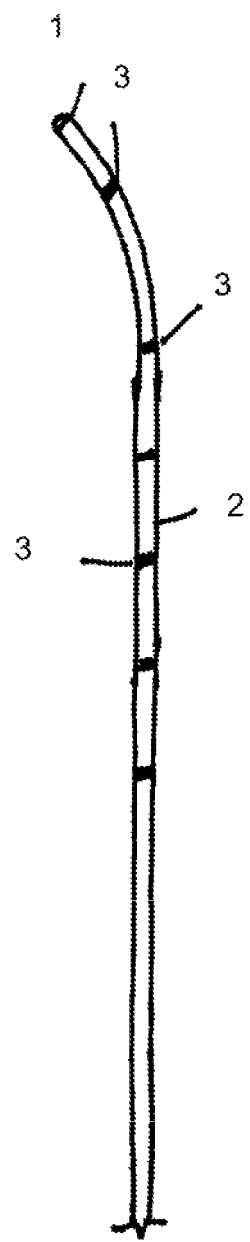
FIG. 2 shows a schematic view of a distal end of the electrophysiological diagnostic catheter.

An electrophysiological diagnostic catheter 10 comprises a manipulation handgrip 7, a main tube 2, a distal ring 1, and diagnostic rings 3. The main tube 2 includes an internal channel 2', electric wires and two connections 8, 9: a connection 8 for bioptome connection and an electrical connection 9.

Figure 3:
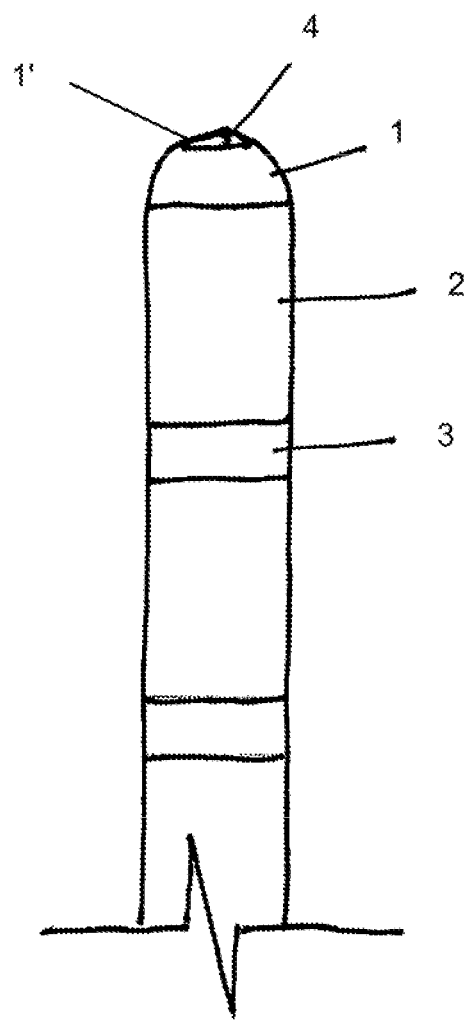
FIG. 3 shows a schematic view from the side of the distal end of electrophysiological diagnostic catheter with inserted bioptome in stand-by mode.
Figure 4:
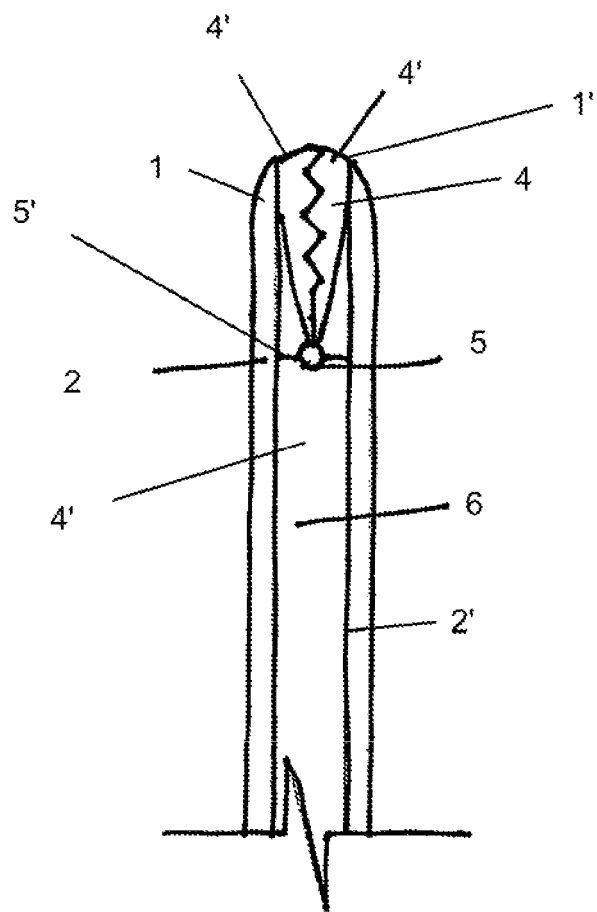
FIG. 4 shows a cross-sectional view of the distal end of the electrophysiological diagnostic catheter with inserted bioptome in stand-by mode.
Figure 5:
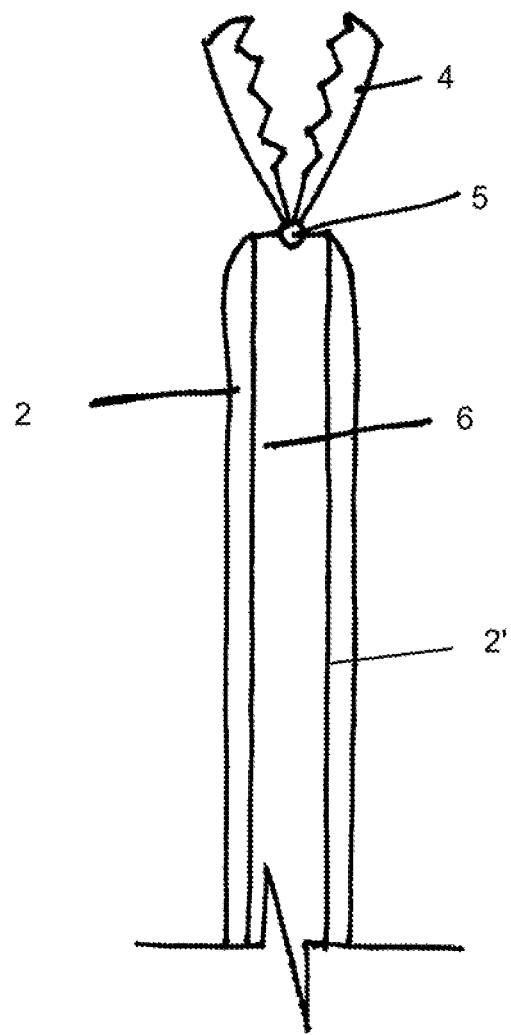
FIG. 5 shows cross-sectional view of the distal end of electrophysiological diagnostic catheter with bioptome in an ejected position with open forceps.
Figure 6:
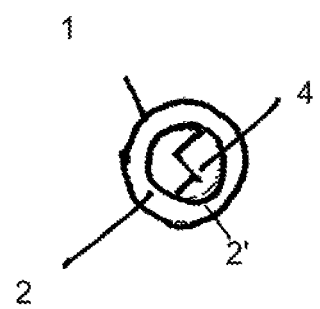
FIG. 6 shows cross-sectional view of the distal end of the electrophysiological diagnostic catheter.

The electrophysiological diagnostic catheter 10 comprises one internal channel 2', which is a centrally located channel being a transmission channel for a microdevice, such as a bioptome 4, which opens through a traumatic distal ring 1. The main tube 2, distal ring 1, and diagnostic rings 3 are shaped with smooth, rounded edges as a rounded arc 1' as shown in FIG. 3 and FIG. 4. Sharp edges could break the blood vessels continuity and increase perforation risk in a deployed configuration.

Internal channel 2' is surrounded by electric wires 3' connecting diagnostic rings 3 and distal ring 1 with manipulation handgrip 7 and transmitting electrophysiological parameters to the electrophysiological system 11.

The electrophysiological diagnostic catheter comprises diagnostic rings 3 present in amount of 4 to 20 (default 10) for analysis of electric parameters of heart and vessels evenly distributed on length of 6 to 14 cm. These rings are located in the vicinity of distal end of the catheter. Those rings enable registration of electrophysiological parameters (shape and amplitude of mono- and bipolar electric potential, impedance), selective stimulation using external stimulator or non-fluoroscopic navigation using three-dimensional system.

Additionally, in the main channel or main tube 2, there are wires 3' placed, which control the distal end of catheter by the electrophysiological system 11.

In the vicinity of the main channel or main tube proximal end, there is a manipulation handgrip 7 located and two connections: connection 8 for bioptome 8 insertion and electrical connection 9. In a preferred embodiment, the connection 8 for bioptome insertion comprises a tee 8', which enables introduction of additional channel to internal channel e.g. comprising valve 8", which enables internal channel flush using saline in order to remove debris after a performed biopsy. The internal channel 2' comprises a centrally located valve 8" for bioptome insertion.

Bioptome on its distal end comprises forceps 4 made of pair of jaws. Jaws during convergence (closed position) create an oval ending as in FIG. 3 protruding from electrophysiological diagnostic catheter. 0.25 to 0.75 cm long forceps are finished with a hinge mechanism, which is attached to the bioptome tube, where the tension member is localized, which allows for bioptome jaws manipulation. Thanks to that, it is possible to create open and closed position of bioptome forceps. In open position forceps protrude out of distal ring of electrophysiological diagnostic catheter for maximal 0.75 cm distance, while span is 0-210 degrees.

Forceps are made of alloy visible in X-rays and with suitable bending and breaking resistance. Preferably, it is an alloy used for other surgical instruments. The bioptome 4' includes a bioptome tube 6 ended with handle closing and opening hinge mechanism 5 The hinge 5 enables an ergonomic closing and opening of forceps and ejecting of whole bioptome from electrophysiological diagnostic catheter as also for its blocking against undesirable ejection. In preferred embodiment forceps in closed position are blocked with blocking mechanism by closing/opening grip in order to avoid ejection and non-planned movement outside the distal end of electrophysiological diagnostic catheter. Manipulation of bioptome forceps 4 with jaws 4' using closing/opening grip is possible due to tendon. In other embodiment there is a thread as a blocking means 5' created on the internal side of internal channel and in the region of hinge mechanism 5 of bioptome, which enables execution of at least half bioptome turn in the internal channel of electrophysiological diagnostic catheter.

The electrophysiological diagnostic catheter is introduced to the patient's peripheral vein vessels (femoral) vein, subclavian vein) and is further passed through main vessels to right cardiac cavities. A controlling system enables for bending of the distal catheter ending, which allows for detailed localization of vessels and heart cavities and navigation. Navigation and localization of catheter positions is performed based on analysis of potentials and electrophysiological parameters by three-dimensional system and non-fluoroscopic navigation (without X-rays). Electrophysiological diagnostic catheters thanks to diagnostic rings 3 enable continuous registration of potentials and construction of virtual electroanatomical map giving an image of examined vessels and cardiac cavities. In a moment, when the operator reaches his goal, that is when reaching the desired location, it is possible to introduce bioptome and obtain tissue samples. Forceps jaws are closing from open position by the tension member. Tissue fragments are evacuated inside of the pincers. Next, the operator pulls the forceps in the closed position into the electrophysiological diagnostic catheter and evacuates it from main channel out of patient's body in an atraumatic way. If there is such a need, internal channels of an electrophysiological diagnostic catheter is flushed using saline solution through a lateral channel delivered to the internal channel, which is closed by a valve.

A proximal gap 8''' in fluid connection with the internal channel 2' is ended with a valve 8'' (diaphragm), which enables insertion of a microdevice.

We claim:

1. An electrophysiological diagnostic catheter to obtain an endomyocardial biopsy of heart tissues and to be guided and monitored by an electroanatomical 3D mapping system, the catheter comprising:
   a main tube being flexible in a deployed configuration and having a distal end and a proximal end;
   a manipulation handgrip on said main tube adjacent said proximal end;
   a plurality of diagnostic rings on said main tube, wherein at least one diagnostic ring is a distal ring at said distal end of said main tube; and
   a bioptome removably engaged to said main tube, said bioptome being comprised of a forceps, a hinge, and a bioptome tube,
   wherein said main tube is comprised of an internal channel with distal opening at said distal ring and a proximal opening as said proximal end, said internal channel being centrally located in said main tube,
   wherein said distal opening is in fluid connection with said proximal opening, and
   wherein said bioptome has a stand-by configuration relative to said main tube with said forceps and said distal ring forming a rounded arc at said distal end.

2. The electrophysiological diagnostic catheter according to claim 1, wherein said rounded arc is atraumatic in said deployed configuration.

3. The electrophysiological diagnostic catheter according to claim 1, further comprising:
   an electric connection in connection with said proximal end of said main tube at said manipulation hand grip; and
   a connection to said internal channel in connection with said proximal end of said main tube at said manipulation hand grip.

4. The electrophysiological diagnostic catheter according to claim 1, wherein said plurality of diagnostic rings number between 4 to 20 diagnostic rings.

5. The electrophysiological diagnostic catheter according to claim 1, wherein said internal channel is surrounded by electric wires within said main tube, said electric wires connecting diagnostic rings and said distal ring with said manipulation handgrip, further comprising:
  an electrophysiological system in communication with said diagnostic rings through said electric wires.

6. The electrophysiological diagnostic catheter according to claim 1, wherein bioptome has a removed configuration with said forceps, hinge, and bioptome withdrawn from said internal channel.

7. The electrophysiological diagnostic catheter according to claim 6, wherein said forceps are comprised of laws forming said rounded arc 1' in said stand-by configuration.

8. The electrophysiological diagnostic catheter according to claim 1, further comprising: a blocking means at said distal end of said main tube and in said internal channel.

9. The electrophysiological diagnostic catheter according to claim 8, wherein said blocking means is comprised of a thread, said bioptome being rotated at least one half turn within said internal channel by said thread so as to allow said forceps to open and close.

10. The electrophysiological diagnostic catheter according to claim 3, further comprising: a valve, and a proximal gap between said valve and said internal channel.

* * * * *